United States Patent [19]
Heaton et al.

[11] Patent Number: 6,108,077
[45] Date of Patent: Aug. 22, 2000

[54] SAMPLE SUPPORT WITH A NON-REFLECTING SAMPLE SUPPORTING SURFACE

[75] Inventors: John D. Heaton, Fremont; Duane C. Holmes, Saratoga, both of Calif.

[73] Assignee: Nanometrics Incorporated, Sunnyvael, Calif.

[21] Appl. No.: 09/209,365

[22] Filed: Dec. 8, 1998

[51] Int. Cl.[7] ........................................... G01J 1/00
[52] U.S. Cl. ................................. 356/213; 356/382
[58] Field of Search ........................... 356/382, 372, 356/355, 357, 381, 371, 213, 239.7, 445, 380; 250/559.27

[56] References Cited

U.S. PATENT DOCUMENTS

| | | | |
|---|---|---|---|
| 3,857,637 | 12/1974 | Obenreder | 356/120 |
| 4,984,894 | 1/1991 | Kondo | 356/382 |
| 5,681,888 | 10/1997 | Nomura et al. | 524/496 |

Primary Examiner—Frank G. Font
Assistant Examiner—Tu T. Nguyen
Attorney, Agent, or Firm—Skjerven, Morrill, MacPherson, Franklin and Friel

[57] ABSTRACT

An optical measurement instrument that detects and analyzes reflected light includes a sample support, such as a wafer supporting chuck, with a sample bearing surface that is configured so as to not reflect light back to the optical measurement instrument. In one embodiment, the sample bearing surface of the sample support is a layer of material that absorbs light in the wavelength or wavelengths being used by the optical measurement instrument. For example, a hard plastic, such as poly-ether-ether-ketone (PEEK), may be used to absorb light in the infrared wavelengths. In another embodiment, the entire sample support may be manufactured from the light absorbing material. In yet another embodiment, the top surface of the sample support is configured with light scattering depressions, which prevent light that is incident on the sample bearing surface from being reflected back to the optical measurement instrument.

19 Claims, 3 Drawing Sheets

SAMPLE SUPPORT WITH A NON-REFLECTING SAMPLE SUPPORTING SURFACE

FIELD OF THE INVENTION

The present invention relates to optical measurement instruments that inspect and measure surface, thin-film, or bulk properties of a sample using characteristics of the infrared light reflected from the sample, and more particularly to the use of a sample support with a sample supporting surface that absorbs or scatters incident light.

BACKGROUND

In the manufacturing of semiconductors, many process steps require the measurement of various characteristics of films grown or deposited on the surface of a substrate or wafer. These characteristics include the film-thickness, the index of refraction, the reflectance, or even the concentration of various implanted atomic or ionic constituents. At times similar data about the substrate or wafer itself may be desired.

The conventional method for measuring films on a substrate, such as a semiconductor wafer, uses infrared light to illuminate one side of the wafer. The infrared light travels through the film and the wafer and is collected by a spectrometer on the other side of the wafer.

Another technique to obtain information related to the characteristics of the film or the substrate is to irradiate the sample with infrared light of one or more wavelengths, and collect the light that is reflected from the sample and any films on its surface. In reflection mode, the sample is supported by a planar surface, such as a wafer support or chuck. The chuck typically has a number of holes or channels, which are used to provide a vacuum for holding the sample on the chuck. In addition, by holding the sample tightly to the planar top surface of the chuck, the sample is held as flat as possible, which optimizes measurements.

In certain instances, a percentage of the incident light of a particular wavelength may penetrate through the films on the sample and through the sample itself. In such an instance, the flat areas of the chuck may specularly reflect a significant amount of the light that is transmitted through the sample and its films and is detected by the optical measurement instrument.

The optical measurement instrument includes a detector positioned above the sample that is used to collect the specularly-reflected light from the film and sample. Unfortunately, the detector also collects the specularly-reflected light from the sample supporting surface of the chuck. The light reflected from the chuck is detrimental to measurement, particularly where the sample supporting surface is not uniformly flat, but has miscellaneous holes and channels. Indeed, as reflected light measurements are made of the sample or its film, unknown quantitative contributions from the supporting chuck will reduce the accuracy or degrade the reliability of the desired measurements.

SUMMARY

An optical measurement instrument that detects and analyzes reflected light includes a sample support, such as a wafer supporting chuck, with a sample bearing surface that is configured so as to not reflect light back to the optical measurement instrument.

In one embodiment, the sample bearing surface of the sample support is a layer of material that absorbs light in the wavelength or wavelengths being used by the optical measurement instrument. For example, a hard plastic, such as poly-ether-ether-ketone (PEEK) or other similar types of plastic, may be used to absorb light in the infrared wavelengths. Light incident from a direction nominally normal of the sample bearing top surface of the support will be absorbed, thereby preventing reflection of the incident light back to the optical measurement instrument.

In another embodiment of the present invention, the entire sample support may be manufactured from the light absorbing material.

In yet another embodiment, the top surface of the sample support is configured with light scattering depressions, which prevent light incident on the sample bearing surface from being reflected back to the optical measurement instrument. Because the detector for the optical measurement instrument must necessarily be located within the cone of incident light, any light that is reflected from the sample bearing top surface beneath the sample, will not be reflected back to the detector of the optical measurement instrument.

Thus, the detector of the optical measurement instrument will receive light reflected back from the sample (including any films on the sample) and will not receive light reflected from the sample support. Consequently, the analysis of the reflected light will be simplified and more accurate.

BRIEF DESCRIPTION OF THE DRAWINGS

The above and other features, aspects, and advantages of the present invention will become better understood with regard to the following description, appended claims, and accompanying figures, where:

DETAILED DESCRIPTION

Figure 1:
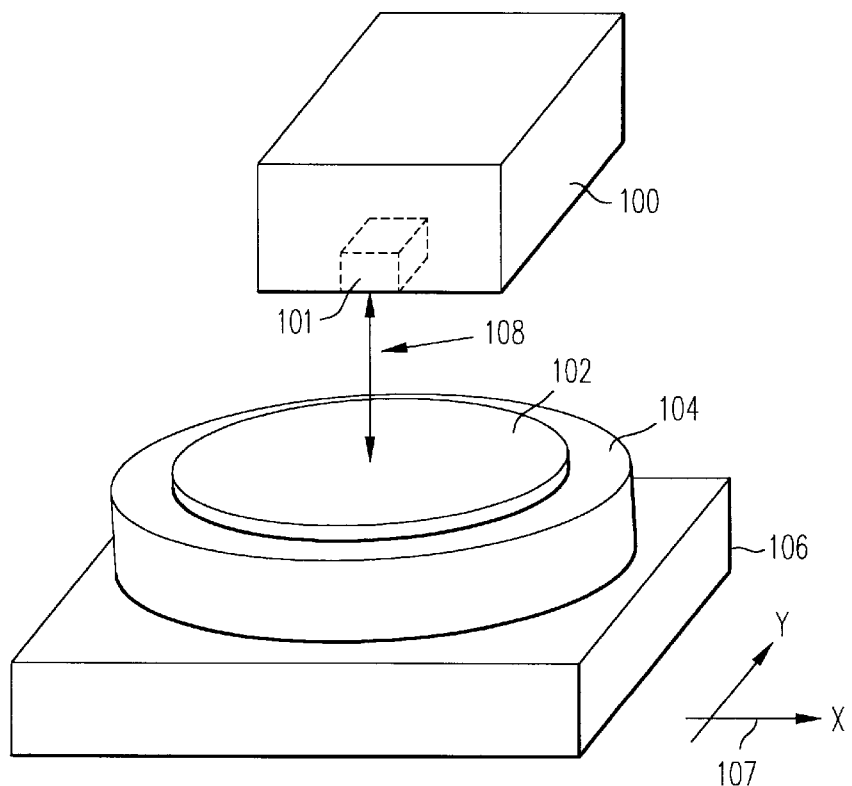
FIG. 1 shows a perspective view of a reflective mode optical measuring instrument positioned over a sample held on a sample support.

FIG. 1 shows a perspective view of a reflective mode optical measurement instrument, such as a Fourier Transform Infrared Spectrometer (FTIR 100), positioned over a sample 102 held on a sample supporting chuck 104. Sample 102 may be a silicon wafer having multiple overlying layers of films or a similar type of sample. Sample 102 is held on chuck 104 using conventional holding methods such as vacuum, edge clips, gravity or electrostatic force.

The FTIR 100 is a system that combines the light source and spectrometer into a single unit to be used in a reflection mode. FTIR 100 may be used to measure characteristics of sample 102, such as film-thickness, the index of refraction, the reflectance, or even the concentration of various implanted atomic or ionic constituents. FTIR 100 directs a beam 108 of infrared light coincident onto sample 102 and any film deposited on sample 102. FTIR 100 includes a detector 101 that detects light reflected from sample 102 and any films. It should be understood that FTIR 100 is intended as merely an example of an optical measurement instrument and not as a limitation. Thus, if desired, other optical measurement instruments may be used. By way of an example, FTIR 100 may be the instrument described in pending U.S. Pat. application Ser. No. 09/113,610, by Duane Holmes, filed on Jul. 10, 1998, and having the same assignee (which is herein incorporated by reference).

As shown in FIG. 1, chuck 104 is mounted on a stage 106 that is conventionally controlled in the X and Y directions, shown by arrows 107, by a microprocessor (not shown) so that the desired measurement area on the sample 102 is accurately positioned under FTIR 100.

Figure 2:
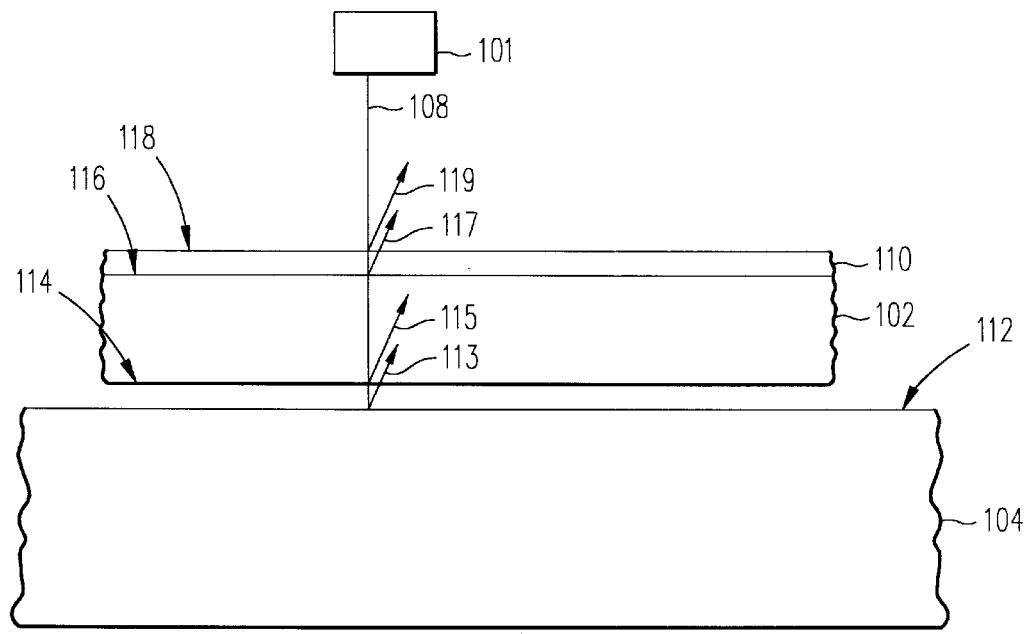
FIG. 2 shows a cross sectional view of a portion of a sample mounted on a portion of a sample supporting chuck along with incident and reflected light beams.

FIG. 2 shows a cross sectional view of a portion of sample 102, with overlying film 110, mounted on a portion of chuck 104. Sample 102 is shown as not contacting the upper surface 112 of chuck 104 because the bottom surface 114 of sample 102 may not be planar and/or chuck 104 includes holes or grooves (not shown), thereby creating a separation between bottom surface 114 of sample and the upper surface 112 of chuck 104. Other areas of sample 102 may be in contact with upper surface 112 at other locations (not shown).

As shown in FIG. 2, beam 108 of light from the FTIR 100 is directed on the film 110 on sample 102. Film 110 has an upper surface 118 and a lower surface that forms the interface 116 between film 110 and the top surface of sample 102. It should be understood that sample 102 is shown with one overlying film 110 for the sake of simplicity, and that sample 102 may have multiple overlying films, resulting in multiple interfaces between films.

As the beam 108 of light is incident on film 110 and sample 102, a percentage of the light passes through film 112 and sample 102 and is absorbed, while a percentage of the light is reflected back to detector 101. As shown in FIG. 2, a percentage of the incident beam 108 is reflected back to the detector 101 off the top surface 118 of film 110 (reflected light 119), more light is reflected off interface 116 between film 110 and sample 102 (reflected light 117), and more light is reflected by the bottom surface 114 of sample 102 (reflected light 115). A portion of the light passes through sample 102 and will be reflected by the top surface 112 of chuck 104 (reflected light 113). It should be understood, that while reflected light 119, 117, 115, and 113 are illustrated as reflecting at non-normal angles from their respective surfaces for clarity, the reflected light actually has an angle of reflection that is equal to the angle of incidence of beam 108, e.g., nominally normal.

Information, such as intensity and wavelength, from the reflected light 119, 117, 115, and 113 received by detector 101 in FTIR 100 is compared to previously determined conventional mathematical models until numerical values can be assigned to the reflected light. The programming of a microprocessor to analyze spectral information obtained by the FTIR 100 is well known to those of ordinary skill in the art, and need not be discussed in detail. However, because the reflected light 119, 117, and 115 from the sample 102 and film 110 surfaces is combined with the reflected light 113 from the sample supporting surface 112 of chuck 104, there is a great deal of complexity and unreliability in the determination of the numerical values. This is particularly true because the sample supporting surface 112 creates strong reflections relative to the reflections that occur at the surfaces of the film and sample.

Figure 3:
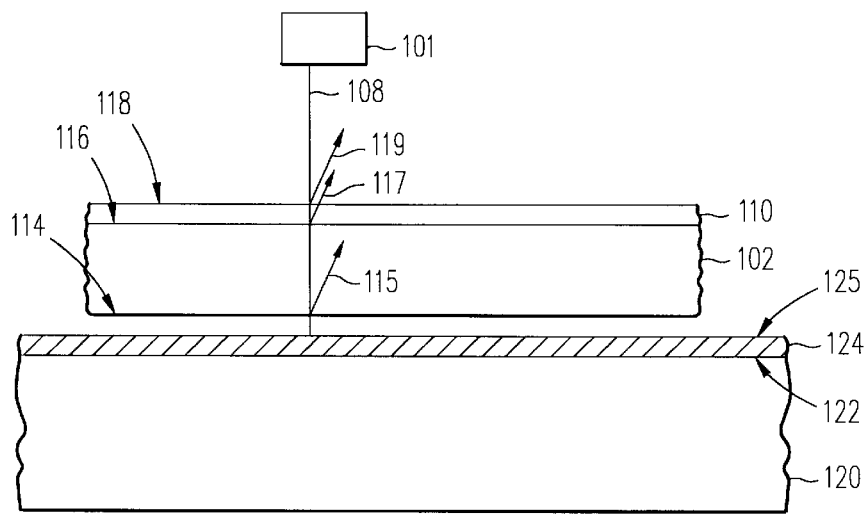
FIG. 3 shows a cross section of a portion of a sample mounted on a chuck, with the sample bearing top surface of the chuck configured to so as to not reflect light back to the optical measurement instrument, in accordance with an embodiment of the present invention.

FIG. 3 shows a cross section of portion of sample 102 having overlaying film 110, mounted on a chuck 120, with sample bearing top surface 125 of chuck 120 configured so as to not reflect light back to detector 101, in accordance with an embodiment of the present invention. As shown in FIG. 3, top surface 122 is covered with a layer of light absorbing material 124 and thus reflected light 113 (shown in FIG. 2) is not present in FIG. 3. Except for the presence of overlying absorbing layer 124, chuck 120 may be the same as and in fact may be used in place of chuck 104 shown in FIGS. 1 and 2, and chuck 120 may be used in place of chuck 104 as shown in FIG. 1.

The absorbing layer 124 may be, for example, an infrared light absorbing plastic material known as PEEK (poly-ether-ether-ketone), manufactured by Dupont, Inc., or other similar type material. Absorbing layer 124 has the property that light incident from a direction nominally normal to its surface will be absorbed, thereby preventing reflection of incident light back to detector 101. For more information relating to PEEK, see U.S. Pat. No. 5,681,888, which is herein incorporated by reference.

It should be understood that while absorbing layer 124 is said to absorb normally incident light, absorbing layer 124 may be used to scatter the light so that only a portion or none of the reflected light will be detected by detector 101. Because any detector of specularly reflected light is located within the cone of incident light, absorbing layer 124 may be used to scatter light outside the cone and thus the light will not be received by the detector.

Chuck 120 is manufactured by removing a layer, for example, 0.25 inches, from the top surface of a conventional chuck and gluing a layer of the absorbing material to the chuck with epoxy or equivalent material, or by mechanically attaching the layer of absorbing material, e.g., with screws, fasteners or the like. Alternatively, a conventional chuck 104 may be coated with a liquid light absorbent material, such as PEEK, which is then permitted to harden. The absorbing material is then conventionally machined to form the desired vacuum channels and/or holes in the top surface. The use of PEEK is particularly advantageous because it is a hard machinable plastic that will produce minimal backside contact contamination. Other materials that may be used as absorbing layer 124 include plastics, such as Vespel, Delrin, both of which are manufactured by Dupont, Inc., or other polymer based materials.

Thus, as shown in FIG. 3, as beam 108 is incident on film 110 and sample 102, reflected light 119, 117, and 115 will still be produced by film 110 and sample 102. The light that passes through sample 102, however, will be incident on the sample bearing top surface 125 and absorbed by absorbing layer 124. In the embodiment in which absorbing layer 124 does not completely absorb, but scatters light outside the cone of incident light, detector 101 will not receive any of the reflected light. Consequently, chuck 120 does not reflect light that will be combined with the light reflected from film 110 and sample 102, thereby simplifying the spectral analysis and providing improved numerical values.

Figure 4:
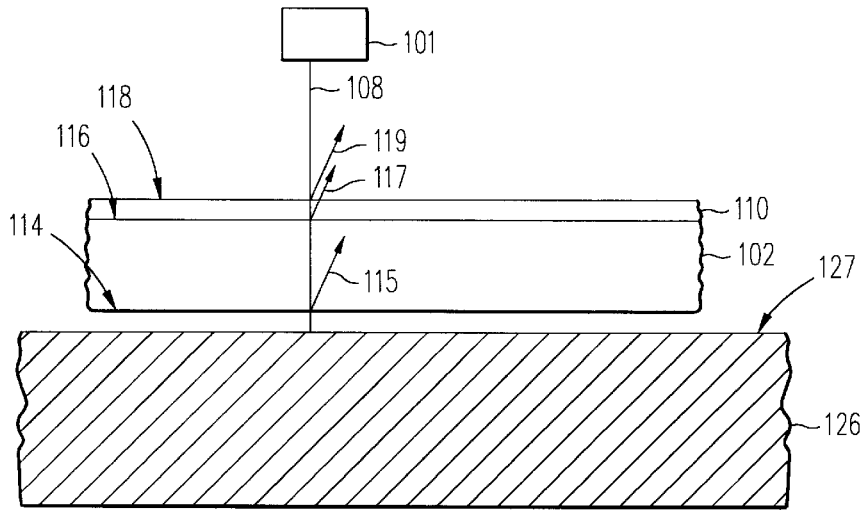
FIG. 4 shows a cross section of a portion of a sample mounted on a chuck, with the sample bearing top surface of the chuck configured to so as to not reflect light back to the optical measurement instrument, in accordance with another embodiment of the present invention.

FIG. 4 shows a cross section of a portion of sample 102, having overlying film 110, mounted on chuck 126 with a sample bearing top surface 127 configured so as to not reflect light back to detector 101, in accordance with another embodiment of the present invention. Chuck 126 is similar to chuck 120 with absorbing layer 124, except that chuck 126 is made entirely from the light absorbing material, such as PEEK or other light absorbing and/or scattering material. As discussed, PEEK is a machinable plastic, and thus the entire chuck 126 may be conventionally machined from this material.

Figure 5:
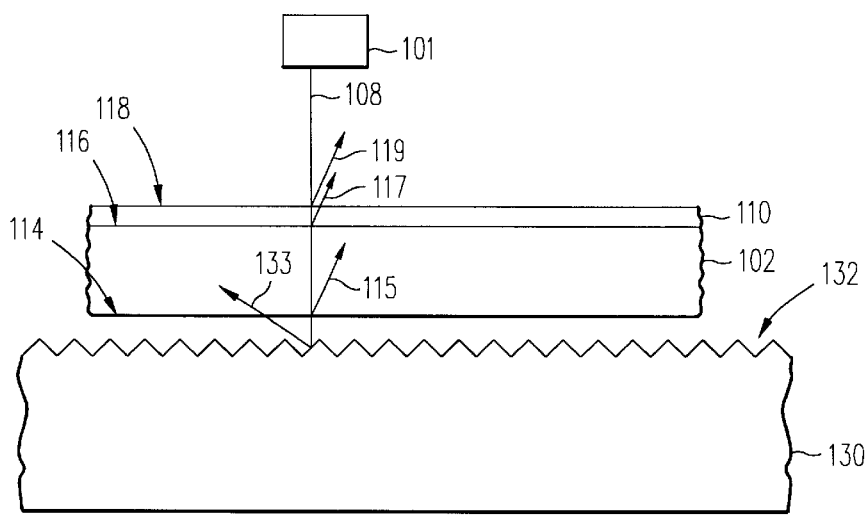
FIG. 5 shows a cross section of a portion of a sample mounted on a chuck, with the sample bearing top surface of the chuck configured to so as to not reflect light back to the optical measurement instrument, in accordance with yet another embodiment of the present invention.

FIG. 5 shows a cross section of a portion of sample 102, having overlying film 110, mounted on a chuck 130 with a sample bearing top surface 132 configured so as to not reflect light back to detector 101, in accordance with another embodiment of the present invention. As shown in FIG. 5, sample bearing top surface 132 has a light scattering configuration. As shown in FIG. 5, top surface 132 includes a series of grooves in a saw tooth type configuration. Thus, light that is normally incident to top surface 132 will be reflected away from detector 101, as indicated by reflected light 133. Thus, top surface 132 scatters incident light away from detector 101 of the FTIR 100. It should be understood, that other types of scattering depressions may be used in place of the series or saw tooth type grooves configuration, including sinusoidal type grooves and a number of dimples.

Figure 6:
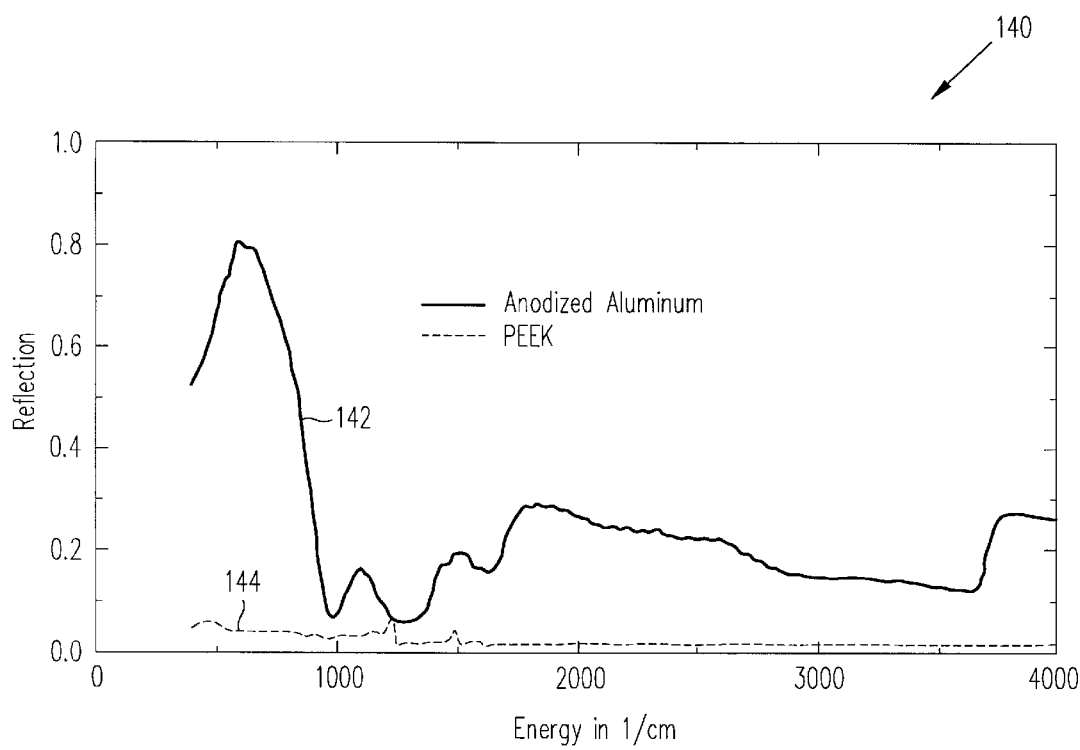
FIG. 6 is a graph showing the spectrum of light generated by reflections from the top surface of conventional anodized aluminum chuck, shown as the dotted line, and the reflections from chuck with an absorbing layer of PEEK, shown as a solid line.

FIG. 6 is a graph 140 showing the spectrum of light generated by reflections from the top surface of conventional anodized aluminum chuck, shown as solid line 142, and the reflections from chuck with an absorbing layer of PEEK, shown as a solid line 144, as measured by a M-series spectrometer from Midac, Inc. The Y axis of graph 140 is the percentage of light that is reflected, while the X axis is a measurement of the wavelength of the infrared light in terms of waves per centimeter. As can be seen in graph 140, the percentage of light that is reflected from the top surface of a conventional chuck is much greater than the percentage of light that is reflected from the top surface of a chuck with an absorbing layer.

Figure 7:
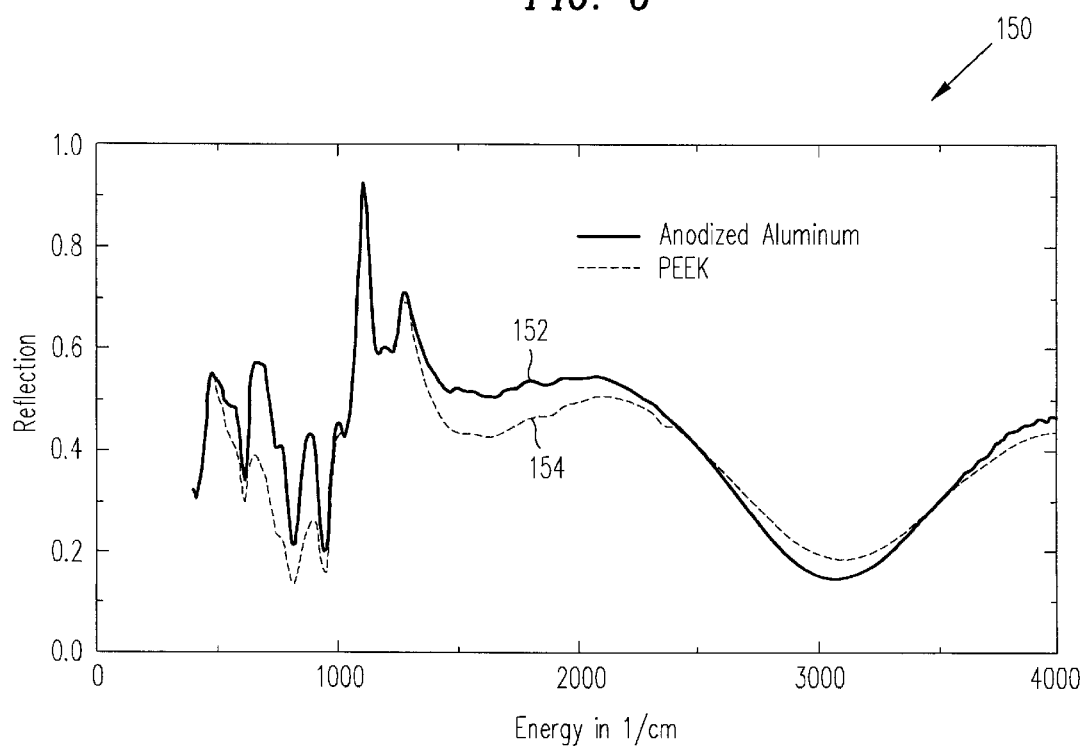
FIG. 7 is a graph showing the spectrum of light generated during the measurement of a sample mounted on a conventional anodized aluminum chuck, as shown by the solid line, and a chuck covered by an absorbing layer of PEEK, as shown by the broken line in a drawing that describes the actual system configuration.

FIG. 7 is a graph 150 showing the spectrum of light generated during the measurement of a sample mounted on a conventional anodized aluminum chuck, as shown by the solid line 152, and a chuck covered by an absorbing layer of PEEK, as shown by the broken line 154, as measured by a M-series spectrometer from Midac, Inc. The sample measured in graph 150 is a 725 micrometer thick silicon substrate with an overlaying 1.75 micrometer thick film of fluorinated silicate glass (FSG). As shown in FIG. 7, the elimination of the reflected light from the sample bearing surface of the chuck lowers the overall signal strength, which will consequently make the small effects caused by the FSG film easier to measure.

Although the present invention has been described in detail, there are other chuck materials that could be used that would absorb the infrared light. The material noted here PEEK has been selected because of its additional benefits for reduced backside contact contamination. Also, the chuck could be coated instead of being fabricated from the described material. Therefore, the spirit and scope of the appended claims should not be limited to the description of the version depicted in the figures or materials noted.

What is claimed is:

1. An apparatus comprising:
    an optical measurement instrument using reflected light to measure properties of one or more films on a sample, said optical measurement instrument having a light source to produce light that is reflected off said one or more films on said sample and a light detector for detecting reflected light, wherein light may be reflected from a bottom surface of said sample; and
    a sample support positioned to hold said sample with one or more films in alignment with said optical measurement instrument, said sample support having a sample bearing top surface, said top surface configured so as to not reflect light to said light detector.

2. An apparatus, as recited in claim 1, wherein said sample bearing top surface comprises:
    a layer of material that absorbs light in the wavelengths used by said optical measurement instrument.

3. An apparatus, as recited in claim 2, wherein said layer of material comprises a plastic.

4. An apparatus, as recited in claim 2, wherein said layer of material comprises poly-ether-ether-ketone (PEEK).

5. An apparatus, as recited in claim 1, wherein said sample support, including said sample bearing top surface, is comprised of a material that absorbs light in the wavelengths used by said optical measurement instrument.

6. An apparatus, as recited in claim 5, wherein said material comprises a plastic.

7. An apparatus, as recited in claim 5, wherein said material comprises polyether-ether-ketone (PEEK).

8. An apparatus, as recited in claim 1, wherein said sample support is used to support a semiconductor wafer.

9. An apparatus comprising:
    an optical measurement instrument using reflected light to measure properties of one or more films on a sample, said optical measurement instrument having a light source to produce light that is reflected off said one or more films on said sample and a light detector for detecting reflected light; and
    a sample support positioned to hold said sample with one or more films in alignment with said optical measurement instrument, said sample support having a sample bearing top surface, said top surface configured so as to not reflect light to said light detector;
    wherein said sample bearing top surface comprises a series of depressions configured to scatter incident light away from said light detector of said optical measurement instrument.

10. An apparatus, as recited in claim 9, wherein said series of depressions are a series of saw tooth type grooves.

11. A sample support for holding a sample with one or more films in alignment with an optical measurement instrument, the optical measurement instrument using reflected light to measure properties of the one or more films on the sample wherein light may be reflected from a bottom surface of said sample, the sample support comprising:
    a sample bearing top surface; and
    means for preventing reflected light from the sample bearing top surface of the sample support from being added to the reflected light from the sample.

12. The sample support, as recited in claim 11, wherein said means comprises said sample bearing top surface being comprised of a material that absorbs light in the wavelengths used by said optical measurement instrument.

13. The sample support, as recited in claim 12, wherein said sample support comprises said material.

14. The sample support, as recited in claim 12, wherein said sample bearing top surface comprises a layer of said material coupled to said sample support.

15. An apparatus, as recited in claim 12, wherein said material comprises polyether-ether-ketone (PEEK).

16. A sample support for holding a sample with one or more films in alignment with an optical measurement instrument, the optical measurement instrument using reflected light to measure properties of the one or more films on the sample, the sample support comprising:

a sample bearing top surface; and means for preventing reflected light from the sample bearing top surface of the sample support from being added to the reflected light from the sample;

wherein said means comprises a series of light scattering depressions in said sample bearing top surface.

17. The sample support, as recited in claim 16, wherein said series of light scattering depressions is a series of saw tooth type grooves.

18. A method of measuring properties of a sample with one or more films using an optical measuring instrument that illuminates the sample and detects and analyzes the reflected light, wherein light may be reflected from a bottom surface of said sample, the method comprising:

placing the sample with one or more films on the top surface of a sample support, said top surface configured so as to not reflect light back to the optical measuring instrument;

illuminating the sample and detecting the reflected light; and analyzing the reflected light from the sample.

19. The method, as recited in claim 18, wherein said top surface is comprised of a material that absorbs light in the wavelengths used by said optical measurement instrument.

* * * * *